United States Patent [19]

Gomarasca et al.

[11] Patent Number: 4,559,345

[45] Date of Patent: Dec. 17, 1985

[54] PYRIMIDINE AND S-TRIAZINE DERIVATIVES WITH ANTILIPIDEMIC ACTIVITY

[75] Inventors: Piero Gomarasca, Cinisello Balsamo; Carlo Scolastico; Cesare Sirtori, both of Milan, all of Italy

[73] Assignee: LBP Istituto Faraceutico S.p.A., Milan, Italy

[21] Appl. No.: 400,434

[22] Filed: Jul. 21, 1982

[30] Foreign Application Priority Data

Aug. 20, 1981 [IT] Italy .................... 23580 A/81

[51] Int. Cl.⁴ ................ C07D 239/46; C07D 239/48; C07D 251/18; A61K 31/505

[52] U.S. Cl. .................... 514/275; 544/320; 544/312; 544/317; 544/321; 544/323; 544/197; 544/208; 544/211; 544/204; 544/210; 544/194; 544/213

[58] Field of Search ............... 544/317, 323, 312, 321; 424/251; 514/275

[56] References Cited

U.S. PATENT DOCUMENTS 3,321,478  5/1967  English et al. .................... 544/326
3,609,136  9/1971  Wegmuller et al. ............... 260/154
3,814,761  6/1974  Santilli et al. ...................... 544/312
3,974,162  8/1976  Santilli et al. ...................... 544/321

OTHER PUBLICATIONS

Reddy et al., *Chem. Abstracts*, 92:175480h, (1980).
Reddy et al., *Chem. Abstracts*, 84:38736s, (1976).

*Primary Examiner*—Donald G. Daus
*Assistant Examiner*—William A. Teoli, Jr.
*Attorney, Agent, or Firm*—Walter H. Schneider

[57] ABSTRACT

Pyrimidine and s-triazine derivatives of formula (I)

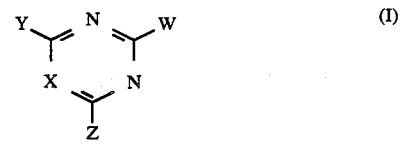

in which X=CH or N; Y=for example halogen, alkoxy; W=for example —S—CH$_2$—COOH, —O—CH$_2$—COO alkyl, —NH—CH$_2$—CONHCH$_2$CH$_2$OH; Z=for example 2,3-xylidino, and methods for the preparation thereof are described. The compounds show high antilipemic activity.

7 Claims, No Drawings

PYRIMIDINE AND S-TRIAZINE DERIVATIVES WITH ANTILIPIDEMIC ACTIVITY

The present invention relates to pyrimidine and s-triazine derivatives with antilipidemic activity, of general formula (I)

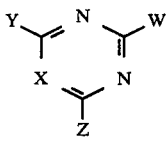

in which:

X is CH or N;

Y is halogen, particularly chlorine; $C_1$-$C_4$ alkoxy; amino;

W is a —Q—$CH_2$—COR; —$NR^1R^2$; —$SR^3$ residue;

Z is one of the following residues:

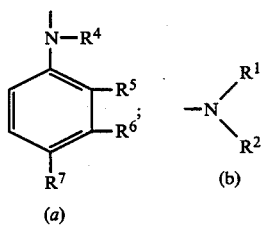

Q is —NH—; —N($CH_3$)—; —O—; —S—;

R is hydroxy; $C_1$-$C_4$ alkoxy; hydrazino; an amino group of formula —$NR^8R^9$;

$R^1$ and $R^2$, each are $C_1$-$C_4$ alkyl groups;

$R^3$ is hydrogen or $C_1$-$C_{10}$ alkyl;

$R^4$ is hydrogen or $C_1$-$C_4$ alkyl;

$R^5$ and $R^6$, which may be the same or different, are hydrogen or methyl;

$R^7$ is hydrogen, $C_1$-$C_4$ alkoxy or trifluoromethyl;

$R^8$ and $R^9$, which may be the same or different, are hydrogen; $C_1$-$C_4$ alkyl; β-mercaptoethyl; —($CH_2$)$_n$OH, where n=1-4.

Another object of this invention are pharmaceutical compositions with hypolipidemic activity, containing one or more compounds of formula (I) as active principle.

The invention concerns moreover processes for the preparation of compounds of formula I. When, in the above formula, X=CH and Y=Cl, the relative compounds may be prepared according to the following synthesis scheme:

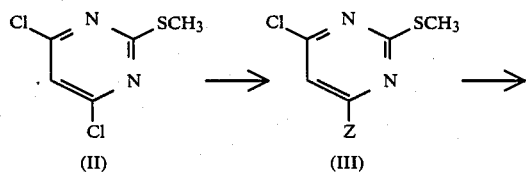

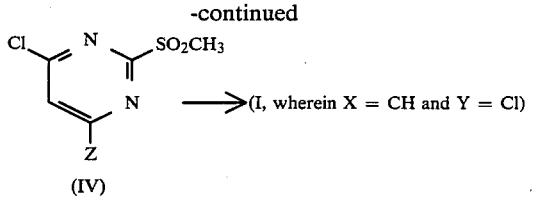

in which Z has the above mentioned meanings.

In other words, 2-methylthio-4,6-dichloro-pyrimidine (II) (H. C. Koppel et al., J. Org. Chemistry 26, 792 (1961)) is reacted with an amine ZH (wherein Z has the meanings (a) or (b) herein above); the so obtained 2-methylthio-4-Z-6-chloropyrimidine (III) is oxidized, for instance with $H_2O_2$ in acetic acid solution and in presence of sodium tungstate, to 2-methylsulfonyl-4-Z-6-chloropyrimidine (IV), from which the final compounds (I, wherein X=CH and Y=Cl) can be prepared by substitution of the methylsulfonyl residue by a residue W.

Generally, such substitution can be carried out with any of the WH compounds (or corresponding W⁻ anions) above described; however, when W represents —Q—$CH_2$—COR, preferably (IV) is reacted with the corresponding compounds in which R is an alkoxy group.

From the so obtained esters can be prepared other pyrimidine derivatives (I) in which R is hydroxy, hydrazino or —$NR^8R^9$ by hydrolysis or, respectively, by hydrazinolysis, or aminolysis with an amine of formula HN$R^8R^9$, wherein $R^8$ and $R^9$ have the above mentioned meanings. Such hydrolysis may be carried out with sodium hydroxide in methanolic or ethanolic solution; also in alcoholic medium may be carried out also the reaction with hydrazine, ammonia or amine.

From the compounds of formula (I) wherein X=CH and Y=Cl, can also be obtained the corresponding compounds in which Y=$C_1$-$C_4$ alkoxy by reaction with metal $C_1$-$C_4$ alkoxydes (e.g. sodium alkoxide) in alcoholic solution, or in presence of crownethers in benzene or acetonitrile, or alternatively by prolonged reaction with alkali metal hydroxides in $C_1$-$C_4$ alcohol solution; similarly, the same compounds (I) wherein X=CH and Y=Cl can be transformed in the corresponding derivatives with Y=amino by treatment with ammonia or amines in slightly more drastic conditions than those used for the above mentioned esters amynolysis.

Moreover, the compounds (I) in which W is —Q—$CH_2$—COR, with R=hydrazino or —$NR^8R^9$ can be prepared starting from the corresponding acids (I, with W=—Q—$CH_2$—COOH) by activation of the latter according to per se known methods (mixed anhydride: N-N'-dicyclohexylcarbodiimide).

Always according to the invention, the compounds of formula (I), wherein X is CH, Y is chlorine and Z is a 2,3-xylidino or N-methyl-2,3-xylidino residue, can be prepared by reaction of a suitable nucleophilic species corresponding to W with 2,4-dichloro-6-(2,3-xylidino)-pyrimidine, respectively with 2,4-dichloro-6-(N-methyl-2,3-xylidino)-pyrimidine, which in turn may be obtained by condensation of 2,4,6-trichloropyrimidine with 2,3-xylidine or with N-methyl-2,3-xylidine, in alcoholic medium.

The hereinafter described 2-(alkyl)-mercapto-4-xylidino (or N-methyl-xylidino)-6-chloropyrimidines can also be obtained by alkylation, with the suitable alkylating species, of the tetrabutyl ammonium salts of thiobarbituric acid, subsequent chlorination by POCl₃ and, finally, substitution with 2,3-xylidine (or N-methyl-2,3-xylidine), according to the following scheme:

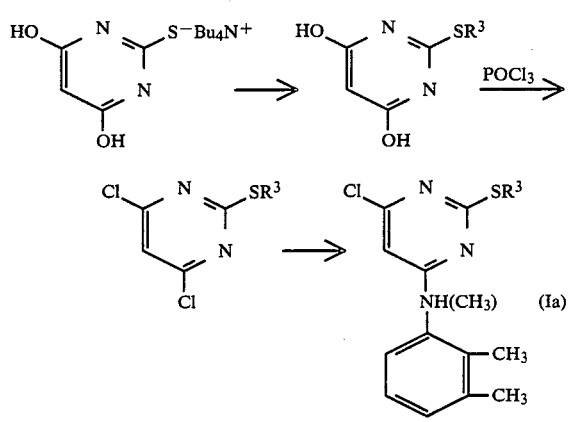

When, as alkylating species, a 4-methoxybenzyl derivative is used, the obtained final compounds (R³=CH₂—C₆H₄—4.OCH₃) can be easily transformed, by treatment with CF₃—COOH and anisole, in the corresponding mercapto compounds (R³=H), which are otherwise difficult to prepare.

The s-triazine compounds of the invention (I, with X=N) can be prepared by reaction of the 2,4-dichloro-6-Z-1,3,5-triazines with suitable nucleophilic species corresponding to the W substituent, for example —S—CH₂COR or HNR¹R². Also for these compounds the substitution of R=alcoxy by other groups (hydroxy, amino etc.) can be carried out after the —Q—CH₂—COR chain has already been inserted on the triazine ring, according to the methods already mentioned for the corresponding pyrimidino compounds. In the same way, the residue Y=Cl can be substituted by Y=alcoxy when on the s.triazine ring is already present the W substituent.

The process according to the invention is further illustrated by the following, not limiting examples.

Examples 1-5 refer to the preparation of intermediates; the subsequent examples describe the preparation of final products of formula I, whose characteristics are summarized in Tables I-V. Numbers between brackets written besides the names of the compounds in examples 6 and following refer to the various tables and to the progressive number of each compound in said tables.

EXAMPLE 1 (intermediates)

(a) 2-Methylthio-4-chloro-6-(2,3-xylidino)-pyrimidine

To a solution of 2-methylthio-4,6-dichloropyrimidine (g 40) in ethanol (400 ml) are added 2,3-xylidine (28.5 ml) and Na₂CO₃ (25 g). The reaction mixture is heated under reflux for 18 hours; then it is filtered and the precipitate is washed with ethanol. By crystallization from the same solvent 26 g of the desired compound are obtained.

M.p. 149°-150° C. (ethanol). With the same method the following intermediates have been prepared:

(b) 2-Methylthio-4-chloro-6-(N-methyl-2,3-xylindino)-pyrimidine

M.p. 121°-123° C. (acetonitrile);

(c) 2-Methylthio-4-chloro-6-anilino-pyridimine

M.p. 116°-118° C. (ethanol);

(d) 2-Methylthio-4-chloro-6-(p-methoxyanilino)-pyrimidine

M.p. 128°-131° C. (methanol/water);

(e) 2-Methylthio-4-chloro-6-(p-trifluoromethylanilino)-pyridimine

M.p. 178°-180° C. (chloroform).

EXAMPLE 2

(a) 2-Methylsulfonyl-4-chloro-6-(2,3-xylidino)-pyrimidine

To the suspension of 2-methylthio-4-chloro-6-(2,3-xylidino)-pyrimidine (34 g, example 1(a)), in glacial acetic acid (340 ml) are added Na₂WO₄ (0.486 g) and a 30% H₂O₂ (43 ml). The reaction mixture is stirred at room temperature for 16 hours. After dilution with water (350 ml) the precipitate is filtered, washed with water to neutrality and dried over CaCl₂, so yielding the desired compound. M.p. 140°-142° C. (ethylacetate/hexane). With the same method the following compounds have been prepared:

(b) 2-Methylsulfonyl-4-chloro-6-(N-methyl-2,3-xylidino)-pyrimidine

M.p. 182°-183° C. (ethylacetate);

(c) 2-Methylsulfonyl-4-chloro-6-anylino-pyrimidine

M.p. 204°-270° C. (ethylacetate/benzene);

(d) 2-Methylsulfonyl-4-chloro-6-(p-metthoxyanilino)-pyrimidine, M.p. 197°-199° C.

(e) 2-Methylsulfonyl-4-chloro-6-(p-trifluoromethylanilino)-pyrimidine

M.p. 184°-186° C. (ethylacetate/hexane).

EXAMPLE 3 (intermediates)

(a) 2,4-Dichloro-6-(2,3-xylidino)-1,3,5-triazine

A solution of cyanuryl chloride (18 g) in hot acetone (70 ml) is poured under stirring into water (40 ml). To the so obtained suspension is added, while keeping the temperature to 5° C., 2,3-xylidine (24 ml). Stirring is maintained for 1 hour at 5° C.; then the reaction mixture is filtered, the precipitate is washed with water to neutrality; it is dissolved in ethyl acetate; the solution is dried over Na₂SO₄. By concentration 16.8 g of the desired compound are obtained. M.p. 186°-188° C. (ethyl acetate/hexane).

With the same method has been prepared:

(b) 2,4-Dichloro-6-(N-methyl-2,3-xylidino)-1,3,5-triazine

M.p. 140°-141° C. (ethyl acetate).

EXAMPLE 4 (intermediates)

2-p-Methoxybenzylthio-4,6-dichloropyrimidine (i) To a suspension of thiobarbituric acid (15 g) in 50% ethanol (180 ml) are added a solution of NaOH (5.1 g) in 50% ethanol (75 ml) and p-methoxybenzyl chloride (18.7 g). The mixture is heated under stirring for 60' at 60° C.; then it is cooled and the solid is filtered by suction, washed with water; then dried over CaCl$_2$, yielding 15 g of 2-p-methoxy-benzylthio-4,6-dihydroxypyrimidine.

(ii) A suspension of 2-p-methoxybenzylthio-4,6-dihydroxypryimidine (45 g) in POCl$_3$ (320 ml) is treated with N,N'-diethylaniline (45 ml) and refluxed for 8 hours. After cooling, the reaction mixture is poured in water/ice and extracted with ethyl acetate; the organic phase is washed to neutrality and dried over Na$_2$SO$_4$. After concentration to small volume and addition of cool hexane, a solid is separed which is filtered by suction. The filtrate is then concentrated to dryness. By distillation under vacuum (174° C. at 0.05 mmHg) 31.5 g of 2-p-methoxybenzylthio-4,6-dichloropyrimidine are obtained. M.p. 48°-49° C. (methanol/water).

EXAMPLE 5 (intermediates)

(a)

2-p-Methoxybenzylthio-4-chloro-6-(2,3-xylidino)-pyrimidine

To a solution of 2-p-methoxybenzylthio-4,6-dichloropyrimidine (19.8 g) in acetonitrile (100 l) is added 2,3-xylidine (16 ml) and the resulting mixture is refluxed for 36 hours. The solid is filtered, washed with a little amount of acetonitrile, then the filtrate is concentrated to dryness. The residue is purified by chromatography on silica-gel. 17 g of the desired product are obtained. M.p. 118°-119° C. (benzene/hexane).

With the same method has been prepared:

(b)

2-p-Methoxybenzylthio-4-chloro-6-(N-methyl-2,3-xylidino)-pyrimidine

M.p. 96°-97° C. (hexane).

EXAMPLE 6

(a)

N-[4-Chloro-6-(2,3-xylidino)-2-pyrimidinyl]-aminoacetic acid, ethyl ester (I, 2)

To a suspensione of sodium hydride (77 mg) in anhydrous tetrahydrofurane (4 ml) NH$_2$CH$_2$CO$_2$C$_2$H$_5$.HCl (477 mg) is added. After stirring at room temperature for 15', triethylamine (0.5 ml) and 2-methylsulfonyl-4-chloro-6-(2,3-xylidino)-pyrimidine (0.5 g) (see ex. (2a)) are added. The reaction mixture is stirred and boiled for 13 hours, then is diluted with water and extracted with ethylacetate; the extract is dried over Na$_2$SO$_4$, and the solvent is evaporated. There are obtained 500 mg of an oil from which, by silica gel chromatography, 218 mg of the desired ester (I, 2) are obtained.

With the same method the following compounds have been prepared:

(b)

N-[4-chloro-6-(N-methyl-2,3-xylidino)-2-pyrimidinyl]-aminoacetic acid, ethyl ester (I, 6)

(c) N-[4-chloro-6-anilino-2-pyrimidinyl]-aminoacetic acid, ethyl ester (I, 9)

(d)

N-[4-chloro-6-(p-methoxyanilino)-2-pyrimidinyl]-aminoacetic acid, ethyl ester (I, 10)

(e)

N-[4-chloro-6-(p-trifluoromethylanilino)-2-pyrimidinyl]-aminoacetic, ethyl ester (I, 11)

EXAMPLE 7

N-[4-chloro-6-(2,3-xylidino)-2-pyrimidinyl]-aminoacetic acid, ethyl ester (I, 2)

(i) to a solution of 2,4,6-trichloropyrimidine (25 g) in ethanol (50 ml) are added 2,3-xylidine (16.6 ml) and anhydrous Na$_2$CO$_3$ (11.5 g). The mixture is stirred at room temperature for 12 hours and then under reflux for others 5 hours. After cooling, the mixture is poured onto water and the solid is filtered and washed with water to neutrality. By crystallization from methylene chloride 27.4 g of 2,4-dichloro-6-(2,3-xylidino)-pyrimidine are obtained.

M.p. 204°-206° C. (CH$_2$Cl$_2$).

(ii) A suspensione of 100% sodium hydride (27 mg) in anhydrous 1,2-dimethoxyethane (1.5 ml) is treated with small amounts of NH$_2$CH$_2$CO$_2$C$_2$H$_5$.HCl (156 mg). Triethylamine (0.16 ml) and 2,4-dichloro-6-(2,3-xylidino)-pyrimidine (300 mg) are added, and the mixture is refluxed for 18 hours. Triethylamine (0.16 ml) is added again, heating under reflux for 24 hours more. Finally, after cooling, the reaction mixture is diluted with water and extracted with methylene chloride. The organic phase is washed to neutrality and dried over Na$_2$SO$_4$. By evaporation of the solvent and crystallization from ethyl acetate 300 mg of ethyl ester of N-[4-chloro-6-(2,3xylidino)-2-pyrimidinyl]-aminoacetic acid (I, 2) are obtained.

EXAMPLE 8

(a)

N-[4-Chloro-6-(2,3-xylidino)-2-pyrimidinyl]-aminoacetic acid (I, 1)

To the suspension of N-[4-chloro-6-(2,3-xylidino)-2-pyrimidinyl]-aminoacetic acid ethyl ester (2.23 g; examples 3a and 5) in ethanol (27 ml) at 60° C., 1N NaOH (13.5 ml) is added, and the mixture is heated for 5'; then diluted with water, evporated under vacuum and extracted with diethyl ether (2×20 ml). After acidification with glacial acetic acid, the precipitate is filtered and washed with water to neutrality. The solid is then dried under vacuum with CaCT$_2$, and 1.9 g of the desired acid are obtained (I, 1). With the same method the following compounds have been prepared:

(b) N-[4-chloro-6-(N-methyl-2,3-xylidino)-2-pyrimidinyl]-aminoacetic acid (I, 5)

(c) [4-chloro-6-(2,3-xylidino)-2-pyrimidinyl]-oxyacetic acid (II, 13)

(d) [4-chloro-6-(N-methyl-2,3-xylidino)-2-pyrimidinyl]-oxyacetic acid (II, 19)

(e) [4-chloro-6-(N-methyl-2,3-xylidino)-2-pyrimidinyl]-thioacetic acid (III, 26)

(f) [4-chloro-6-dimethylamino-2-pyrimidinyl]-thioacetic acid (III, 30)

(g) N-methyl-N-[4-chloro-6-(2,3-xylidino)-2-s.triazinyl]aminoacetic acid (V, 41)

(h) [4-chloro-6-(2,3-xylidino)-2-s.triazinyl]-oxyacetic acid (V, 46)

EXAMPLE 9

(a) [4-Chloro-6-(2,3-xylidino)-2-pyrimidinyl]-oxyacetic acid, ethyl ester (II, 12)

To a suspension of 2-methylsulfonyl-4-chloro-6-(2,3-xylidino)-pyrimidine (4 g) in ethyl glycolate (8 ml) 100% sodium hydride (0.45 g) are added under stirring, keeping the temperature under 45° C. The reaction mixture is stirred at room temperature for 30', cooled at 0° C., then diluted with water. The so separated solid is filtered, washed with water, then dried over $CaCl_2$.4.1G of the desired ester (II, 12) are obtained.

With the same method the following compounds have been prepared:

(b) ethyl [4-chloro-6-(N-methyl-2,3-xylidino)-2-pyrimidinyl]oxyacetate (II, 18)

(e) ethyl [4-chloro-6-anilino-2-pyrimidinyl]-oxyacetate (II, 22)

(e) ethyl [4-chloro-6-(p-methoxyanilino)-2-pyrimidinyl]oxyacetate (II, 23)

(e) ethyl [4-chloro-6-(p-trifluoromethylanilino)-2-pyrimidinyl]oxyacetate (II, 24)

EXAMPLE 10

[4-Chloro-6-(N-methyl-2,3-xylidino)-2-pyrimidinyl]-thioacetic acid, ethyl ester (III, 25)

To a suspensione of ethyl 4,6-dichloro-2-pyrimidinyl-thioacetate (10.7 g) in ethanol (100 ml) anhydrous $NaCO_3$ (4.66 g) and N-methyl-2,3-xylidine (6.2 g) are added; the mixture is refluxed under stirring for 24 hours.

After filtrating and concentrating the filtrate, 5 g of the desired ester (III, 25) are obtained.

EXAMPLE 11

[4-Chloro-6-dimethylamino-2-pyrimidinyl]-thioacetic acid, ethyl ester (III, 29)

A solution of ethyl 4,6-dichloro-2-pyrimidinylthioacetate (6 g) in acetonitrile (25 ml) is treated with a 33% aqueous solution of dimethylamine (6.4 ml). The mixture is left to stand at room temperature for 1 hour, then is cooled for 2 hours at 0° C. The precipitate is filtered, washed with a small quantity of acetonitrile: 4.85 g of the desired product are obtained (III, 29).

EXAMPLE 12

(a) 2-Dimethylamine-4-chloro-6-(2,3-xylidino)-pyrimidine (IV, 38)

To a solution of triethylamine (13.8 ml) in benzene (150 ml) a 33% aqueous solution of $(CH_3)_2NH$ (13.5 ml and 2-methylsulfonyl-4-chloro-6-(2,3-xylidino)-pyrimidine (15 g) are added, and the mixture is stirred at room temperature for 16 hours. The organic phase is washed with $H_2O$, dried over $NaSO_4$ and concentrated to dryness under reduced pressure. The residue is purified by chromatography on silica-gel, yielding 7.2 g of the desired compound (IV, 38).

By the same method the following compound has been prepared:

(b) 2-dimethylamine-4-chloro-6-(N-methyl-2,3-xylidino)-pyrimidine (IV, 39)

EXAMPLE 13

(a) 2-Dimethylamine-4-chloro-6-(2,3-xylidino)-pyrimidine (IV, 38)

To a suspension of 2,4-dichloro-6-(2,3-xylidino)-pyrimidine (10 g) in ethanol (70 ml) $Na_2CO_3$ (7 g) and dimethylamine as 40% aqueous solution (5.2 ml) are added. The mixture is refluxed for 18 hours. After cooling and diluting with water, a solid is separated and filtered, purified by chromatography on silica and crystallized from methanol, yielding 7 g of the desired compound (IV, 38).

With the same method, starting from cyanuryl chloride, the following compound has been prepared:

(b) 2-dimethylamine-4-chloro-6-(2,3-xylidino)-s-triazine (V, 47)

EXAMPLE 14

(a) N-[4-Chloro-6-(2,3-xylidino)-2-pyrimidinyl]-aminoacetic acid amide (I, 3)

A suspension of ethyl 4-chloro-6-(2,3-xylidino)-2-pyrimidinylaminoacetate (500 mg) in a 10% ammonia ethanolic solution (5 ml) is heated for 20 hours at 120° C. in closed vessel. The mixture is then diluted with water (10 ml) and filtered, yielding 300 mg of the desired amide (I, 3). By the same method the amides of the following acids have been prepared:

(b) N-[4-(chloro-6-(N-methyl-2,3-xylidino)-2-pyrimidinyl]-aminoacetic (I, 7)

(c) [4-Chloro-6-(2,3-xylidino)-2-pyrimidinyl]-oxyacetic (II, 14)

(d) [4-Chloro-6-(N-methyl-2,3-xylidino)-2-pyrimidinyl]oxyacetic (II, 20)

(e) [4-chloro-6-(N-methyl-2,3-xylidino)-2-pyrimidinyl]-thioacetic (III, 27)

(f) [4-chloro-6-(dimethylamino)-2-pyrimidinyl]-thioacetic (III, 31)

EXAMPLE 15

[4-Chloro-6-(2,3-xylidino)-2-pyrimidinyl]-oxyacetic acid hydrazide (II, 17)

To a solution of ethyl [4-chloro-6-(2,3-xylidino)-2-pyrimidinyl]-oxyacetate (240 mg) in ethanol (2 ml), at room temperature, under stirring, hydrazine hydrate is added (0.3 ml). After 3' the precipitated solid is filtered and recrystallized from ethanol, yielding 100 mg of the desired hydrazide (II, 17).

EXAMPLE 16

(a) N-β-Hydroxyethylamide of [4-ethoxy-6-(2,3-xylidino)-2-pyrimidinyl]-thioacetic acid (III, 37)

A suspension of [4-ethoxy-6-(2,3-xylidino)-2-pyrimidinyl]-thioacetic acid (0.5 g) in anhydrous and ethanol-free chloroform (5 ml) is treated with triethylamine (0.25 ml), then cooled to −5° C. and treated dropwise with a solution of isobutyl chloroformiate (0.25 ml) in chloroform (1 ml).

A solution of ethanolamine (0.10 ml) in chloroform (1 ml) is then added. The temperature is left to raise to 10° C., maintaining this value for 15 hours. Then the solvent is evaporated, the residue is diluted with ethyl acetate and washed with a saturated NaHCO₃-solution (2×20 ml) and water. The organic phase is dried over Na₂SO₄ and the solvent is evaporated giving 150 g of crude product which is purified by chromatography on silica gel to yield 520 mg of pure III, 37.

By the same method the following compounds have been prepared:

(b) [4-chloro-6-dimethylamino-2-pyrimidinyl]-thioacetic acid, N-β-hydroxyethylamide (III, 32)

(c) [4-ethoxy-6-(2,3-xylidino)-2-triazinyl]-thioacetic acid, N-β-hydroxyethylamide (V, 49)

(d) [4-chloro-6-(N-methyl-2,3-xylidino)-2-pyrimidinyl]-oxyacetic acid, N-β-hydroxyethylamide (II, 21)

(e) [4-chloro-6-(2,3-xylidino)-2-pyrimidinyl]-oxyacetic acid, N-β-hydroxyethylamide (II, 15)

and moreover:

(f) [4-ethoxy-6-(2,3-xylidino)-2-s-triazinil]-thioacetic acid amide (V, 48)

(g) [4-chloro-6-(2,3-xylidino)-2-pyrimidinyl]-oxyacetic acid N-butylamide (II, 16)

EXAMPLE 17

(a) N-β-Hydroxyethylamide of [4-chloro-6-(N-methyl-2,3-xylidino)-2-pyrimidinyl]-thioacetic acid (III, 28)

To the solution of [4-chloro-6-(N-methyl-2,3-xylidino)-2-pyrimidinyl]-thioacetic acid (0.5 g) in CH₂Cl₂ (2.5 ml), at −5° C., mg 305 of N,N'-dicyclohexyl-carbodiimide in 2 ml of CH₂Cl₂ are added. After stirring for 15 minutes at −5° C., 0.09 ml of ethanolamine are added. The temperature is then raised to 20° C. in 1 hour. The mixture is filtered, and the solvent is evaporated. The solution of the residue is ethyl acetate is washed with a saturated NaHCO₃ solution, then with water. The raw product is purified by chromatography on SiO₂, yielding 160 mg of the title compound (III, 28).

By the same method, the following compound has been prepared:

(b) N-β-hydroxyethylamide of N-[4-chloro-6-(N-methyl-2,3-xylidino)-2-pyrimidinyl]-aminoacetic acid (I, 8)

EXAMPLE 18

N-β-Hydroxyethylamide of N-[4-chloro-6-(2,3-xylidino)-2-pyrimidinyl]aminoacetic acid (I, 4)

A solution of thriethylphosphine (430 mg) in carbon tetrachloride (2 ml) and tetrahydrofurane (6 ml) is boiled for 30' under stirring. After cooling at 5° C., N-[4-chloro-6-(2,3-xylidino)-2-pyrimidinyl]-aminoacetic acid (0.5 g) is added; after 10' ethanolamine (0.2 ml) is added and the solution is boiled for 3 hours. The solvents are then evaporated, the residue is treated with ethyl acetate, washed twice with a saturated NaHCO₃ solution and then with water, and dried over Na₂SO₄. By evaporation of the solvent an oil (720 mg) is obtained from which, by chromathography on silica, 250 mg of the desired hydroxyethylamide (I, 4) are obtained.

EXAMPLE 19

(a) [4-Chloro-6-(2,3-xylidino)-2-s.triazinyl]-thioacetic acid, ethyl ester (V, 42)

To a suspension of 100% sodium hydride (1 g) in anhydrous 1,2-dimethoxyethane (40 ml) 2,4-dichloro-6-(2,3-xylidino)-1,3,5-triazine (10 g; see example 3) and then, dropwise, ethyl thioglycolate (4.4 ml), are added, maintaining the temperature below 25° C. The reaction mixture is stirred at room temperature for 30', then is refluxed for 12 hours. The separated NaCl is filtered and washed with hot 1,2-dimethoxyethane (50 ml). The solvent is evaporated and the crude product is purified by chromatography on silica, yielding 6 g of the desired compound (V, 42). By the same method, using the suitable reactants, the following compounds have been prepared:

(b) [4-chloro-6-(2,3-xylidino)-2-s-triazinyl]-oxyacetic acid, ethyl ester (V, 45);

(c) N-methyl-N-[4-chloro-6-(2,3-xylidino)-2-s-triazinyl]-aminoacetic acid, ethyl ester (V, 40).

EXAMPLE 20

[4-Ethoxy-6-(2,3-xylidino)-2-s-triazinyl]thioacetic acid (V, 44)

To a suspension of ethyl 4-chloro-6-(2,3-xylidino)-2-s.triazinyltioacetate (14.5 g) in ethanol (150 ml) 1N NaOH (88 ml) is added at 60° C., and the mixture is boiled for 20'. After cooling, the ethanol is evaporated, the residue is acidificated with concentrated HCl and washed with water to neutrality. Drying under vacuum on CaCl$_2$, yields 13.5 g of acid (V, 44).

EXAMPLE 21

[4-Chloro-6-(2,3-xylidino)-2-s-triazinyl]-thioacetic acid (V, 43)

To a solution of thioglycolic acid (0.076 ml) in hexamethylphosphortriamide (2 ml), 100% sodium hydride (46 mg) is added, at room temperature, stirring for 15'. Then 2,4-dichloro-6-(2,3-xylidino)-1,3,5-triazine (0.26 g) in hexamethylphosphorotriamide (1.5 ml) is added, stirring for 30' more. The reaction mixture is then diluted with ethyl ether (15 ml), added with 10% HCl (7 ml) and stirred for 10'. The orgaic phase is separated, washed with water to neutrality and dried over Na$_2$SO$_4$. By evaporation of the solvent an oil (0.24 g) is obtained which crystallizes from ethyl acetate/hexane. Yield: 0.18 g of the title compound (V, 43).

EXAMPLE 22

2-Octylthio-4-chloro-6-(2,3-xylidino)-pyrimidine (III, 35)

(i) To a solution of tetrabutylammonium hydroxide (40% in water, 20 g) thiobarbituric acid (4 g) is added at room temperature. The reaction mixture is stirred for 10' and diluted with chloroform. The separated solid is filtered and dried under vacuum over CaCl$_2$, yielding 9.5 g of tetrabutylammonium salt of thiobarbituric acid.

To a solution of the same salt (16 g) in methanol (240 ml) 1-iodooctane (40 ml) is added. The reaction mixture is refluxed for 8 hours, cooled, concentrated to small volume and diluted with water. The separated residue is treated firstly with acetone and then with ethyl acetate. Filtration yields 7.6 g of 2-octylthio-4,6-dihydroxipyrimidine.

(ii) 2-Octylthio-4,6-dihydroxypyrimidine (6.5 g) is added under stirring to POCl$_3$ (50 ml); the mixture is refluxed for 8 hours. Then the excess of POCl$_3$ is distilled, the resulting residue is poured in water/ice (150 ml) and extracted with ethyl acetate. The organic phase is washed with a saturated aqueous NaCl solution to neutrality and dried over Na$_2$SO$_4$; the solvent is evaporated. Silica gel chromatography yields 5.8 g of pure 2-octylthio-4,6-dichloropyrimidine (oil).

(iii) To a solution of 2-octylthio-4,6-dichloropyrimidine (3 g) in ethanol (25 ml), 2,3-xylidine (1,5 ml) and anhydrous Na$_2$CO$_3$ (1.25 g) are added; the mixture is refluxed for 20 hours. The residue is hot filtered and the solvent is evaporated. The residue is purified by chromathography on silica gel, yielding 1.9 g of 2-octylthio-4-chloro-6-(2,3-xylidino)-pyrimidine (III, 35).

EXAMPLE 23

(a) 2-Mercapto-4-chloro-6-(2,3-xylidino)-pyrimidine (III, 33)

To a suspension of 2-p-methoxybenzylthio-4-chloro-6-(2,3-xylidino)-pyrimidine (8 g; see example 5) in trifluoroacetic acid (80 ml) anisole (2,7 ml) is added and the mixture is refluxed for 50'. After cooling, the trifluoroacetic acid is evaporated. The residue is dissolved in ethyl ether and the separated solid is filtered, washed with ethyl ether, then with water to neutrality, with cool acetone and again with ethyl ether. 5 G of the desired product (III, 33) are obtained.

By the same method has been prepared the following compound:

(b) 2-mercapto-4-chloro-6-(N-methyl-2,3-xylidino)-pyrimidine (III, 36)

The following Tables I–V show some characteristics of the compounds, whose preparation has been described in the examples hereinabove. The structure of said compounds has been confirmed in most cases according to IR and NMR spectra, which have not been reported here for sake of shortness.

TABLE I

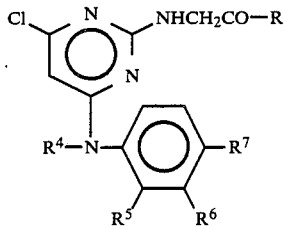

| No | R | R$^4$ | R$^{5-6}$ | R$^7$ | M.p. (°C.) | Cryst. solvent | Raw formula | Elemental analysis calc. | found |
|---|---|---|---|---|---|---|---|---|---|
| 1 | OH | H | CH$_3$ | H | 205–206 | EtOAc | C$_{14}$H$_{15}$N$_4$O$_2$Cl | C 54.79<br>H 4.93<br>N 18.27 | 54.56<br>4.75<br>18.00 |
| 2 | OC$_2$H$_5$ | H | CH$_3$ | H | 164–166 | EtOAc | C$_{16}$H$_{19}$N$_4$O$_2$Cl | C 57.37<br>H 5.72<br>N 16.74 | 57.50<br>5.62<br>16.60 |
| 3 | NH$_2$ | H | CH$_3$ | H | 209–211 | EtOAc/<br>C$_6$H$_6$ | C$_{14}$H$_{16}$N$_5$OCl | C 54.97<br>H 5.28<br>N 22.92 | 54.81<br>5.20<br>22.79 |
| 4 | NH(CH$_2$)$_2$OH | H | CH$_3$ | H | 176–178 | EtOAc | C$_{16}$H$_{20}$N$_5$O$_2$Cl | C 54.91<br>H 5.77<br>N 20.03 | 55.17<br>5.94<br>20.13 |
| 5 | OH | CH$_3$ | CH$_3$ | H | 170–172 | EtOAc/<br>hexane | C$_{15}$H$_{17}$N$_4$O$_2$Cl | C 56.14<br>H 5.34 | 56.20<br>5.18 |

TABLE I-continued

Structure:
Cl-[pyrimidine with N, N]-NHCH$_2$CO-R
with R$^4$-N substituent on pyrimidine connected to phenyl ring bearing R$^5$, R$^6$, R$^7$

| No | R | R$^4$ | R$^{5-6}$ | R$^7$ | M.p. (°C.) | Cryst. solvent | Raw formula | Elemental analysis calc. | found |
|---|---|---|---|---|---|---|---|---|---|
| 6 | OC$_2$H$_5$ | CH$_3$ | CH$_3$ | H | 154–156 | EtOAc | C$_{17}$H$_{21}$N$_4$O$_2$Cl | N 17.47 / C 58.53 / H 6.07 | 17.23 / 58.58 / 6.10 |
| 7 | NH$_2$ | CH$_3$ | CH$_3$ | H | 186–188 | EtOH | C$_{15}$H$_{18}$N$_5$OCl | N 16.06 / C 56.31 / H 5.68 | 16.00 / 56.13 / 5.76 |
| 8 | NH(CH$_2$)$_2$OH | CH$_3$ | CH$_3$ | H | 204–205 | EtOAc/MeOH | C$_{17}$H$_{22}$N$_5$O$_2$Cl | N 21.91 / C 56.12 / H 6.09 | 21.85 / 56.14 / 6.23 |
| 9 | OC$_2$H$_5$ | H | H | H | 179–182 | EtOAc | C$_{14}$H$_{15}$N$_4$O$_2$Cl | N 19.25 / C 54.79 / H 4.93 | 19.12 / 54.57 / 4.77 |
| 10 | OC$_2$H$_5$ | H | H | OCH$_3$ | 171–173 | EtOAc/hexane | C$_{15}$H$_{17}$N$_4$O$_3$Cl | N 18.27 / C 53.47 / H 5.09 | 18.13 / 53.65 / 4.86 |
| 11 | OC$_2$H$_5$ | H | H | CF$_3$ | 273–239 | EtOAc | C$_{15}$H$_{14}$N$_4$O$_2$ClF$_3$ | N 16.65 / C 48.08 / H 3.76 / N 14.95 | 16.88 / 47.95 / 3.64 / 14.65 |

TABLE II

Structure:
Cl-[pyrimidine with N, N]-NHCH$_2$CO-R
with R$^4$-N substituent on pyrimidine connected to phenyl ring bearing R$^5$, R$^6$, R$^7$

| No | R | R$^4$ | R$^{5-6}$ | R$^7$ | M.p. (°C.) | Cryst. solvent | Raw formula | Elemental analysis calc. | found |
|---|---|---|---|---|---|---|---|---|---|
| 12 | OC$_2$H$_5$ | H | CH$_3$ | H | 96–98 | EtOAc/hexane | C$_{16}$H$_{18}$N$_3$O$_3$Cl | C 57.20 / H 5.40 / N 12.52 | 57.66 / 5.47 / 12.47 |
| 13 | OH | H | CH$_3$ | H | 190–191 | Acetone | C$_{14}$H$_{14}$N$_3$O$_3$Cl | C 54.61 / H 4.58 / N 13.66 | 54.75 / 4.82 / 13.40 |
| 14 | NH$_2$ | H | CH$_3$ | H | 211–212 | EtOH | C$_{14}$H$_{15}$N$_4$O$_2$Cl | C 54.79 / H 4.93 / N 18.27 | 54.53 / 5.03 / 18.17 |
| 15 | NH(CH$_2$)$_2$OH | H | CH$_3$ | H | 191–192 | EtOAc | C$_{16}$H$_{19}$N$_4$O$_3$Cl | C 54.76 / H 5.46 / N 15.98 | 54.56 / 5.47 / 15.78 |
| 16 | NHC$_4$H$_9$ | H | CH$_3$ | H | 128–129 | EtOAc/hexane | C$_{18}$H$_{23}$N$_4$O$_2$Cl | C 59.56 / H 6.39 / N 15.45 | 59.36 / 6.29 / 15.30 |
| 17 | NHNH$_2$ | H | CH$_3$ | H | 182–184 | EtOH | C$_{14}$H$_{16}$N$_5$O$_2$Cl | C 52.23 / H 5.01 / N 21.78 | 52.13 / 5.09 / 21.50 |
| 18 | OC$_2$H$_5$ | CH$_3$ | CH$_3$ | H | 101–103 | EtOAc/hexane | C$_{17}$H$_{20}$N$_3$O$_3$Cl | C 58.34 / H 5.76 / N 12.20 | 58.60 / 5.57 / 11.97 |
| 19 | OH | CH$_3$ | CH$_3$ | H | 154–155 | EtOAc | C$_{15}$H$_{16}$N$_3$O$_3$Cl | C 55.96 / H 5.02 / N 13.07 | 56.09 / 4.88 / 13.02 |
| 20 | NH$_2$ | CH$_3$ | CH$_3$ | H | 207–209 | EtOH | C$_{15}$H$_{17}$N$_4$O$_2$Cl | C 56.14 / H 5.34 / N 17.48 | 56.26 / 5.47 / 17.66 |
| 21 | NH(CH$_2$)$_2$OH | CH$_3$ | CH$_3$ | H | 132–134 | EtOAc | C$_{17}$H$_{21}$N$_4$O$_3$Cl | C 55.94 / H 5.80 / N 15.37 | 55.74 / 5.75 / 15.17 |
| 22 | OC$_2$H$_5$ | H | H | H | 135–137 | EtOAc/ | C$_{14}$H$_{14}$N$_3$O$_3$Cl | C 54.64 | 54.38 |

TABLE II-continued

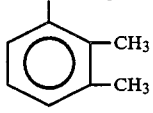

| No | R | R⁴ | R⁵⁻⁶ | R⁷ | M.p. (°C.) | Cryst. solvent | Raw formula | Elemental analysis calc. | found |
|----|---|----|----|----|----|----|----|----|----|
|  |  |  |  |  |  | hexane |  | H 4.58 | 4.40 |
|  |  |  |  |  |  |  |  | N 13.65 | 13.74 |
| 23 | $OC_2H_5$ | H | H | $OCH_3$ | 143–146 | MeOH | $C_{15}H_{16}N_3O_4Cl$ | C 53.32 | 53.23 |
|  |  |  |  |  |  |  |  | H 4.78 | 4.67 |
|  |  |  |  |  |  |  |  | N 12.45 | 12.37 |
| 24 | $OC_2H_5$ | H | H | $CF_3$ | 199–202 | EtOAc | $C_{15}H_{13}N_3O_3ClF_3$ | C 47.95 | 47.83 |
|  |  |  |  |  |  |  |  | H 3.49 | 3.39 |
|  |  |  |  |  |  |  |  | N 11.18 | 11.21 |

TABLE III

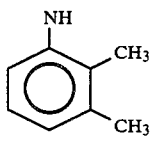

| No | A | Y | Z | M.p. (°C.) | Cryst. solvent | Raw formula | Elemental analysis calc. | found |
|----|---|---|---|----|----|----|----|----|
| 25 | $CH_2CO_2C_2H_5$ | Cl | N-CH₃, 2,3-(CH₃)₂-phenyl | 78–80 | EtOAc | $C_{17}H_{20}N_3O_2SCl$ | C 55.80 | 55.40 |
|  |  |  |  |  |  |  | H 5.51 | 5.46 |
|  |  |  |  |  |  |  | N 11.49 | 11.35 |
| 26 | $CH_2CO_2H$ | Cl | " | 174–176 | EtOAc/hexane | $C_{15}H_{16}N_3O_2SCl$ | C 53.30 | 53.27 |
|  |  |  |  |  |  |  | H 4.27 | 4.66 |
|  |  |  |  |  |  |  | N 12.44 | 12.29 |
| 27 | $CH_2CONH_2$ | Cl | " | 123–126 | EtOH/$H_2O$ | $C_{15}H_{17}N_4OSCl$ | C 53.46 | 53.31 |
|  |  |  |  |  |  |  | H 5.09 | 5.00 |
|  |  |  |  |  |  |  | N 16.64 | 16.84 |
| 28 | $CH_2CONH(CH_2)_2OH$ | Cl | " | 140–142 | EtOAc | $C_{17}H_{21}N_4O_2SCl$ | C 53.61 | 53.62 |
|  |  |  |  |  |  |  | H 5.56 | 5.75 |
|  |  |  |  |  |  |  | N 14.71 | 14.58 |
| 29 | $CH_2CO_2C_2H_5$ | Cl | $N(CH_3)_2$ | 97–98 | $CH_3CN$ | $C_{10}H_{14}N_3O_2SCl$ | C 43.53 | 43.70 |
|  |  |  |  |  |  |  | H 5.11 | 5.01 |
|  |  |  |  |  |  |  | N 15.24 | 15.00 |
| 30 | $CH_2CO_2H$ | Cl | " | 187–189 | Acetone | $C_8H_{10}N_3O_2SCl$ | C 38.76 | 38.95 |
|  |  |  |  |  |  |  | H 4.07 | 4.17 |
|  |  |  |  |  |  |  | N 16.97 | 17.09 |
| 31 | $CH_2CONH_2$ | Cl | " | 203–205 | EtOAc | $C_8H_{11}N_4OSCl$ | C 38.92 | 38.80 |
|  |  |  |  |  |  |  | H 4.50 | 4.46 |
|  |  |  |  |  |  |  | N 22.72 | 22.49 |
| 32 | $CH_2CONH(CH_2)_2OH$ | Cl | " | 137–139 | EtOAc | $C_{10}H_{15}N_4O_2SCl$ | C 41.28 | 41.16 |
|  |  |  |  |  |  |  | H 5.20 | 5.16 |
|  |  |  |  |  |  |  | N 19.38 | 19.24 |
| 33 | H | Cl | NH-(2,3-dimethylphenyl) | >250 | $Et_2O$ | $C_{12}H_{12}N_3SCl$ | C 54.23 | 54.10 |
|  |  |  |  |  |  |  | H 4.55 | 4.50 |
|  |  |  |  |  |  |  | N 15.81 | 15.90 |
| 34 | $CH_3$ | Cl | " | 149–150 | EtOH | $C_{13}H_{14}N_3SCl$ | C 55.91 | 56.05 |
|  |  |  |  |  |  |  | H 5.01 | 5.28 |
|  |  |  |  |  |  |  | N 15.05 | 15.08 |
| 35 | $n\text{-}C_8H_{17}$ | Cl | " | (oil) | — | $C_{20}H_{28}N_3SCl$ | C 63.66 | 63.95 |
|  |  |  |  |  |  |  | H 7.42 | 7.40 |
|  |  |  |  |  |  |  | N 11.10 | 10.89 |

TABLE III-continued $$\text{structure: pyrimidine with Y, Z substituents and S-A group}$$

| No | A | Y | Z | M.p. (°C.) | Cryst. solvent | Raw formula | Elemental analysis calc. | found |
|---|---|---|---|---|---|---|---|---|
| 36 | H | Cl | N-CH3 attached to 2,3-dimethylphenyl | >290 | EtOAc/Et2O | $C_{13}H_{14}N_3SCl$ | C 55.81<br>H 5.04<br>N 15.02 | 55.95<br>5.22<br>14.92 |
| 37 | $CH_2CONH(CH_2)_2OH$ | Cl | NH-2,3-dimethylphenyl | 112–114 | EtOAc/petrol ether | $C_{18}H_{24}N_4O_3S$ | C 57.43<br>H 6.42<br>N 14.88 | 57.19<br>6.29<br>14.90 |

TABLE IV

Structure: pyrimidine with Cl, N(CH3)2, and B-linked 2,3-dimethylphenyl group

| No | B | M.p. (°C.) | Cryst. solvent | Raw formula | Elemental analysis calc. | found |
|---|---|---|---|---|---|---|
| 38 | NH | 146–147 | EtOAc/hexane | $C_{14}H_{17}N_4Cl$ | C 60.73<br>H 6.19<br>N 20.25 | 60.80<br>6.32<br>20.02 |
| 39 | NCH3 | 99–101 | hexane | $C_{15}H_{19}N_4Cl$ | C 61.93<br>H 6.58<br>N 19.27 | 61.88<br>6.52<br>19.16 |

TABLE V

Structure: triazine with Y, W, and NH-2,3-dimethylphenyl substituents

| No | W | Y | M.p. (°C.) | Cryst. solvent | Raw formula | Elemental analysis calc. | found |
|---|---|---|---|---|---|---|---|
| 40 | $N(CH_3)CH_2CO_2C_2H_5$ | Cl | 92–93 | EtOAc | $C_{16}H_{20}N_5O_2Cl$ | C 54.94<br>H 5.76<br>N 20.02 | 55.10<br>5.84<br>19.91 |
| 41 | $N(CH_3)CH_2CO_2H$ | Cl | 185–186 | Acetone | $C_{14}H_{16}N_5O_2Cl$ | C 52.23<br>H 5.01<br>N 21.77 | 52.00<br>5.12<br>21.70 |
| 42 | $SCH_2CO_2C_2H_5$ | Cl | 69–71 | EtOAc/hexane | $C_{15}H_{17}N_4O_2SCl$ | C 51.04<br>H 4.85<br>N 15.88 | 51.20<br>5.02<br>15.67 |
| 43 | $SCH_2CO_2H$ | Cl | 215 dec. | EtOAc/hexane | $C_{13}H_{13}N_4O_2SCl$ | C 48.05<br>H 4.03<br>N 17.25 | 48.20<br>4.13<br>17.07 |
| 44 | $SCH_2CO_2H$ | $OC_2H_5$ | 220–221 | Acetone | $C_{15}H_{18}N_4O_3S$ | C 53.89<br>H 5.38<br>N 16.76 | 54.06<br>5.50<br>16.70 |
| 45 | $OCH_2CO_2C_2H_5$ | Cl | 80–82 | EtOAc/hexane | $C_{15}H_{17}N_4O_3Cl$ | C 53.47<br>H 5.09<br>N 16.64 | 53.28<br>5.01<br>16.79 |

TABLE V-continued

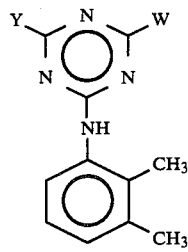

| No | W | Y | M.p. (°C.) | Cryst. solvent | Raw formula | Elemental analysis calc. | found |
|---|---|---|---|---|---|---|---|
| 46 | OCH$_2$CO$_2$H | Cl | 171–173 | EtOAc | C$_{13}$H$_{13}$N$_4$O$_3$Cl | C 50.55<br>H 4.24<br>N 18.15 | 50.80<br>4.41<br>18.35 |
| 47 | N(CH$_3$)$_2$ | Cl | 167–168 | EtOAc | C$_{13}$H$_{16}$N$_5$Cl | C 56.19<br>H 5.80<br>N 25.22 | 56.35<br>5.61<br>25.39 |
| 48 | SCH$_2$CONH$_2$ | OC$_2$H$_5$ | 205–207 | EtOAc | C$_{15}$H$_{19}$N$_5$O$_2$S | C 54.01<br>H 5.75<br>N 21.02 | 53.98<br>5.66<br>21.13 |
| 49 | SCH$_2$CONH(CH$_2$)$_2$OH | OC$_2$H$_5$ | 151–153 | EtOAc | C$_{17}$H$_{23}$N$_5$O$_3$S | C 54.09<br>H 6.14<br>N 18.55 | 54.35<br>6.32<br>18.81 |

The compounds according to the invention have been investigated in order to ascertain their activity against the clinical and experimental hyperlipidemias. More particularly, the following aspects have been taken into consideration:

(1) Evaluation of the hypolipidemic activity in the standard diet test in normal rats (Buchanan, Jour. Med. Chem., 12/6, 1001, 1969), by administering per os the compound to be tested for 4 days and subsequently determining the cholesterolaemia, triglyceridaemia and high density lipoproteins (HDL) levels.

(2) Activity of some of the molecules, which resulted particularly active in the preliminary screenings, in the induced diet hyperlipidemia test (Nath, Jour. Nutr. 67, 289, 1959) and on the lipolysis induced by ACTH and fast.

(3) Examination of the lipoprotein composition, with particular regard to the HDL plasma concentration, both in the presence of the standard diet and the hyperlipidic diet.

(4) Preliminary examination of the weight of the liver and of its hystological characteristics (conventional and electronic microscopy) with some of the most promising compounds.

It is known that drugs like Clofibrate are capable of inducing peroxisomal proliferation in the hepatocytes which, on a long term, may lead to neoplastic hyperplasias (Reddy et al. Nature, 283, 397, 1980).

All the tests have been carried out on male Sprague-Dawley rats of average weight of 200–250 g.

As the comparison substances, there have been selected the [4-chloro-6-(2,3-xylidyno)-2-pyrimidinyl]-thioacetic acid (Wy-14,643; A. A. Santilli et al., Experientia, 30, 1110, 1974), the corresponding ethanolamide (pyrinixil; Sirtori et al., Atherosclerosis, 26, 79, 1977) and the metformin (dimethylbiguanide) (Sirtori et al., Atherosclerosis, 30, 45, 1978). The choice of the comparison substance has been made on the basis of the structural characteristics of the molecules: in the case of the pyrimidine-like compounds bearing at the 2-position a thioacetic substituent, Wy-14,643 has been selected as the comparison product, whereas the activity of pyrinixil has been compared with that of compound III, 37. On the other hand, the metformin has been essentially employed in comparison with the compounds having a triazine ring or bearing a dimethylamino group at the 2-position. Wy 14,643 and pyrinixil, as well as the related compounds, were tested at 50 mg/kg, the metformin and the related compound at 200 mg/kg. The peroxisomal investigation have been carried out on Fisher rats. The data obtained in the test by Buchanan have been reported in Tables VI→IX, which also indicate the structural characteristics of the compounds. Some of them have displayed substantially remarkable hypolipidemic properties by essentially acting on the triglyceridaemia and the α-lipoproteins or HDL, which represent the main anti-atherosclerotic lipoproteic fraction in the blood plasma (Miller and Miller, ii, 16, 1975). As a consequence of this preliminary activity, it has been decided to investigate more in depth certain molecules which seemed to be the most promising ones. These molecules have been screened in the hyperlipidic diet test by determining both lipidaemia and weight of the liver, and, moreover, in some lipolysis tests. Compounds I,1, IV,38 and III,37 have shown to possess a marked hypolipidemic action in the hyperlipidic diet test according to Nath (see above). Dosages ranging from about 6.25 and 25 mg/kg of compounds I1 and III,37 and from about 50 to about 200 mg/kg of compound IV,38 were able to reduce the haematic triglycerides content from about 13.5 to about 38% over the controls, whereas the reduction of the haematic cholesterol varied from about 8.7 to about 25% over the controls, depending on the employed dosages. It is of great importance to stress the fact that in this test none of the three above tested compounds has caused any increase of the weight of the liver: compounds I,1 and IV,38 do not give raise to any significant variation of the hepatic volume (+5%, +2%, −4% and +5%, +5%, and −0.1% respectively at the three employed doses), whereas a moderate increase (+8%, +9% and +17%) was observed with compound III,37, especially when tested at the highest dose.

In order to better investigate the hepatomegalic effect of these representative compounds of the invention, they were administered to Fisher rats (F-344) which show the highest sensitivity to the peroxisomal and hepatocarcinogenic proliferating action (Reddy et al., Arch. Pharmacodyn. Ther., 234, 414, 1978). It has been found that compound III,37 has no influence on the hepatic volume and the peroxisomes, when examined by the electronic microscopy in Fisher rats; a similar lack of increase of hepatic peroxisomes proliferation has been also displayed by compounds I,1 and IV,38. Compound I,1 promotes the functions of the enzymes peroxisomal-catalase and enoyl-CoA-hydratase. In this test, all the compounds were administered for 6–8 weeks admixed with the diet in a weight proportion of 0.2%.

Finally, the anti-lipolytic activity of these three substances was investigated against ACTH (100 U/kg) and against the liplytic effect of a 24-hours fast. None of the compounds has shown any relevant action against ACTH, whereas all of them have proved to be active against the fast induced lipolysis, by reducing the increase of free fatty acids of a percent value varying from about 23 to about 35 percent over the controls.

The obtained pharmacological results confirm that the compounds according to the present invention are very interesting at the level of the hypolipidemic activity, the lipoproteic modifications and the action on the hepatic structures. In general, the invention compounds possess a more remarkable action against the hypertriglyceridaemia than against the hypercholesterolaemia. Of particular interest, is the effect on the high-density lipoproteins (HDl or α-lipoproteins) induced by the major part of the compounds. It can be supposed that this effect is mediated by an activation of the lipoproteinlipase, which favors the mobilization of the cholesterol from the tissues (Nikkila et al., Metabolism, 26, 179, 1977). Anyway, the most important observation is that the compounds according to the present invention do not cause any proliferation of the liver peroxisomes, thus being devoid of those hypothetic carcinogenic risks which recently have repeatedly been pointed out with respect to clofibrate-like products (WHO Study, Brit. Heart. Jour., 40, 1069, 1978). The lack of significantly toxic side-effects—based on preliminary data of acute and subacute toxicity—makes these compounds as potentially very interesting in the treatment of hyperlipoproteinaemia and in the prevention of the atherosclerosis.

TABLE VI

Compounds with pyrimidine-like structure containing sulfur. For all of the compounds bearing in A the carboxy group, the corresponding free and substituted amides were synthetized: the activity is the same, the toxicity is substantially lower

| Code | A | Z | Comparison substance | Dose mg/kg | Cholesterol | HDL | Triglycerides |
|---|---|---|---|---|---|---|---|
| III, 33 | H | NH-(2,3-dimethylphenyl) | Metformin | 200 | −21.6 | +14.7 | −15.6 |
|  |  |  |  | 200 | −12.0 | +6.4 | +0.5 |
| III, 36 | H | N(CH₃)-(2,3-dimethylphenyl) | Metformin | 200 | +5.2 | −1.1 | −21.6 |
|  |  |  |  | 200 | +7.0 | −1.9 | +1.3 |
| III, 34 | CH₃ | " | Wy-14,643 | 50 | −13.1 | +5.3 | −10.5 |
|  |  |  |  | 50 | −21.8 | +11.8 | −31.7 |
| III, 35 | C₈H₁₇ | " | Wy-14,643 | 50 | −17.3 | −2.9 | −14.6 |
|  |  |  |  | 50 | −20.5 | +5.0 | −29.6 |
| III, 26 | CH₂CO₂H | N(CH₃)-(2,3-dimethylphenyl) | Wy-14,643 | 50 | −15.4 | +7.2 | −39.1 |
|  |  |  |  | 50 | −22.9 | +6.3 | −30.6 |
| III, 30 | CH₂CO₂H | N(CH₃)₂ | Wy-14,643 | 50 | −13.3 | +4.0 | −32.9 |
|  |  |  |  | 50 | −29.7 | +4.5 | −34.9 |
| III, 37* | CH₂CONH(CH₂)₂OH | NH-(2,3-dimethylphenyl) | Pirinixil | 50 | −38.9 | +10.1 | −55.2 |
|  |  |  |  | 50 | −45.9 | +12.3 | −60.4 |

*This compound possess an ethoxy group instead of the chlorine atom at the 4-position.

TABLE VII

Compounds with pyrimidine-like structure in which the sulfur atom is substituted by a nitrogen or an oxygen atom.
For all of the compounds bearing in W the carboxy group, the corresponding free and substituted amides were synthetized: the activity the same, the toxicity is substantially lower

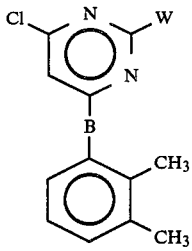

| Code | W | B | Comparison substance | Dose mg/kg | Cholesterol | HDL | Triglycerides |
|---|---|---|---|---|---|---|---|
| I, 1 | NHCH₂CO₂H | NH | Wy-14,643 | 50 | −12.5 | +9.8 | −37.8 |
|  |  |  |  | 50 | −19.0 | +13.3 | −25.0 |
| I, 5 | NHCH₂CO₂H | NCH₃ | Wy-14,643 | 50 | −20.9 | +22.0 | −49.4 |
|  |  |  |  | 50 | −27.5 | +10.3 | −44.9 |
| II, 13 | OCH₂CO₂H | NH | Wy-14,643 | 50 | −17.1 | +19.7 | −38.0 |
|  |  |  |  | 50 | −19.8 | +13.3 | −15.0 |
| II, 19 | OCH₂CO₂H | NCH₃ | Wy-14,643 | 50 | −14.3 | n.s. | −23.3 |
|  |  |  |  | 50 | −30.4 | n.s. | −0.3 |

TABLE VIII

Compounds with pyrimidin-like structure similar to metformin

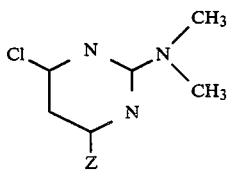

| Code | Z | Comparison substance | Dose mg/kg | Cholesterol | HDL | Triglycerides |
|---|---|---|---|---|---|---|
| IV,38 | NH-(2,3-dimethylphenyl) | Metformin | 200 | −9.4 | +9.8 | −35.3 |
|  |  |  | 200 | −6.6 | +15.0 | −5.6 |
| IV,39 | N(CH₃)-(2,3-dimethylphenyl) | Metformin | 200 | −8.9 | +2.8 | −14.6 |
|  |  |  | 200 | −10.0 | +6.4 | −14.5 |
| 1004* | N(CH₃)₂ | Metformin | 200 | +65.9 | +0.5 | −39.2 |
|  |  |  | 200 | +7.0 | −1.9 | +1.3 |
| 1006* | NH₂ | Metformin | 200 | −3.6 | +17.0 | −25.8 |
|  |  |  | 200 | −4.9 | +8.6 | +11.3 |

*These two molecules are already known from the literature: W. R. Boon, JCS, 1532 (1952).

TABLE IX

Compounds with triazine structure
(For all the compounds bearing in W the carboxy group, the corresponding free and substituted amides were synthetized: the activity is the same, the toxicity is substantially lower).

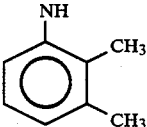

| Code | W | Y | Z | Comparison substance | Dose mg/kg | Cholesterol | HDL | Triglycerides |
|---|---|---|---|---|---|---|---|---|
| V,41 | N(CH₃)CH₂COOH | Cl | 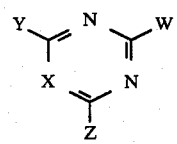 | Metformin | 200 | −6.1 | +8.0 | −35.6 |
|  |  |  |  |  | 200 | −2.7 | +2.6 | −16.9 |
| V,44 | SCH₂CO₂H | OC₂H₅ | " | Metformin | 200 | −12.3 | +9.3 | −42.4 |
|  |  |  |  |  | 200 | −2.7 | +2.8 | −16.9 |
| V,47 | N(CH₃)₂ | Cl | " | Metformin | 200 | −7.5 | +5.5 | −30.8 |
|  |  |  |  |  | 200 | −3.1 | +3.8 | −16.9 |
| 1000* | N(CH₃)₂ | Cl | N(CH₃)₂ | Metformin | 200 | −1.9 | +10.9 | −43.3 |
|  |  |  |  |  | 200 | −2.7 | +2.8 | −16.9 |
| 1006* | N(CH₃)₂ | Cl | NH₂ | Metformin | 200 | +42.5 | +14.3 | −35.4 |
|  |  |  |  |  | 200 | −4.9 | +8.6 | +11.3 |

*These two molecules are already known from the literature: W. M. Pearlman and C. K. Banks, JACS, 70, 3726,1948.

We claim:

1. Compounds of formula I,

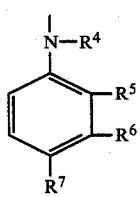

in which
X is CH;
Y is halogen;
W is Q—CH₂—COR;
Z is

N—R⁴ attached to a benzene ring with R⁵, R⁶, R⁷ substituents;

Q is NH, N(CH₃);
R is OH, C₁–C₄ alkoxy, hydrazino or NR⁸R⁹;
R⁴ is H or C₁–C₄ alkyl;
R⁵ and R⁶, which may be equal or different, are H or CH₃;
R⁷ is H, C₁–C₄ alkoxy or CF₃;
R⁸ and R⁹, which may be equal or different, are H, C₁–C₄ alkyl, β-mercaptoethyl, or (CH₂)ₙOH, where n=2–4.

2. A compound as claimed in claim 1 which is N-[4-chloro-6-(2,3-xylidino)-2-pyrimidinyl]-aminoacetic acid.

3. A compound as claimed in claim 1 which is the ethyl ester of N-[4-chloro-6-(2,3-xylidino)-2-pyrimidinyl]-aminoacetic acid.

4. A compound as claimed in claim 1 which is the amide of N-[4-chloro-6-(2,3-xylidino)-2-pyrimidinyl]-aminoacetic acid.

5. A compound as claimed in claim 1 which is the N-β-hydroxyethylamide of N-[4-chloro-6-(2,3-xylidino)-2-pyrimidinyl]-aminoacetic acid.

6. A compound of the formula

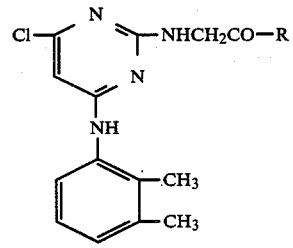

in which
R=OH, C₁–C₄ alkoxy or NR⁸R⁹ in which R⁸ and R⁹ are the same or different and are H or (CH₂)ₙOH where n is 2–4.

7. Pharmaceutical compositions with hypolipidemic activity, comprising an effective amount of one or more compounds as claimed in claim 1, together with a compatible, pharmaceutically acceptable carrier or coating.

* * * * *